United States Patent [19]
Srinivasan et al.

[11] 4,104,124
[45] Aug. 1, 1978

[54] PROCESS FOR THE PRODUCTION OF SINGLE CELL PROTEIN AND AMINO ACIDS

[75] Inventors: Vadake R. Srinivasan, Baton Rouge, La.; Ye-Chin Choi, Athens, Ga.

[73] Assignee: Louisiana State University Foundation, Baton Rouge, La.

[21] Appl. No.: 718,974

[22] Filed: Aug. 30, 1976

[51] Int. Cl.$^2$ .......................... C12B 1/00; C12D 13/06
[52] U.S. Cl. ......................................... 195/33; 195/47; 195/96; 195/112; 195/32
[58] Field of Search ............... 195/28 R, 32, 33, 36 R, 195/37, 47, 96, 112

[56] References Cited

U.S. PATENT DOCUMENTS

| | | | |
|---|---|---|---|
| 3,308,035 | 3/1967 | Douros | 195/28 R |
| 3,761,355 | 9/1973 | Callihan et al. | 195/33 |

OTHER PUBLICATIONS

Mandels et al., "Enhanced Cellulose Production by a Mutant of *Trichoderma viride*", Applied Microbiology Jan. 1971, pp. 152–154.
Han et al., "Single Cell Protein from Cellulosic Wastes", Food Technology vol. 25, 1971 pp. 32–35 & 56.

*Primary Examiner*—R. B. Penland
*Attorney, Agent, or Firm*—Llewellyn A. Proctor

[57] ABSTRACT

A process for the production, by spontaneous or induced mutations from a parent microorganism of the genus Cellulomonas (ATCC-21399), of selected mutants which have the ability to excrete L-glutamic acid or L-lysine, or both, inclusive particularly of certain of the mutant strains produced by the mutagenesis, to wit: Cellulomonas sp. ATCC-21399 strain LC-10, Cellulomonas sp. ATCC-21399 strain A$^r$-1, and Cellulomonas sp ATCC-21399 strain A$^r$-156. In a preferred process comestible, digestible protein is produced from these strains in an aqueous culture medium, or broth, which contains an assimilable source of carbon, particularly cellulose, nitrogen and mineral nutrients. The mutant strains are comparable with the parent organism in cellulolytic activity and growth rate, but the nutritional requirements, notably the need of a yeast extract, are far less exacting than for the parent microorganism, or microorganisms.

14 Claims, No Drawings

PROCESS FOR THE PRODUCTION OF SINGLE CELL PROTEIN AND AMINO ACIDS

The staggering food deficit, particularly the problem of protein deficiency now faced by many nations, and the possibility of its spread, even to the industrial nations, has stimulated efforts to produce microbial, single-cell protein by fermentation processes. Processes for the biosynthesis of protein of high metabolic quality from various carbon energy sources have become well known over the last two decades. An important process for the biosynthesis of protein is described by reference to U.S. Pat. No. 3,761,355 to C. D. Callihan et al which issued Sept. 25, 1973; the disclosure of which is herewith incorporated by reference.

The patent describes a process for the preparation of comestible, digestible protein from cellulose, inclusive of agricultural and urban waste cellulosic materials, by cultivation of the cellulose in an aqueous medium, or culture broth, with a cellulase-elaborating microorganism of the genus *Cellulomonas* (ATCC-21399). In an initial step, a cellulose substrate is ground to small size and formed into an aqueous slurry which is alkali-treated, generally with sodium hydroxide, at elevated temperature for a time sufficient to decrystallize and delignify the cellulose. The alkali-treated cellulose, generally after washing, is then fed into a fermentor and the aqueous fermentation medium, containing the nutrients required for growth, is inoculated with the microorganism, or possibly a symbiotic admixture of such microorganisms, suitably *Cellulomonas* and *Candida guilliermondii* or *Trichosporon cutaneum*. During fermentation, the medium is continuously stirred, the temperature is maintained at from about 25° to about 40° C, and the medium is aerated with air (oxygen) while the pH is maintained at between about 5 and 9. At the end of the fermentation period, normally from about 4 to 8 hours, the biomass is withdrawn from the fermentor as a slurry, flocculant is added to coalesce the cells and the slurry is filtered. The microorganism as single-cell protein is thus harvested for direct use as a food, or used as a food supplement.

This process has offered numerous advantages over most prior art fermentation processes, notably in that it uses a plentiful, low cost or waste material as a carbon source from which it produces quality metabolic protein, i.e., protein which contains all of the amino acids necessary for growth, maintainance and reproduction in a balance suitable for efficient use. This is of profound importance, because in the past, high-quality protein has been supplied almost entirely by meat, milk, fish, eggs and poultry. Moreover, the process is one wherein high cellulolytic activity is achieved, and the rate of growth of the parent microorganism is rapid. Despite these admirable characteristics of the process, however, the nutritional requirements of the microorganism are somewhat exacting. In such process, yeast extract is used as a portion of the medium for achieving rapid growth of the microorganism. A process which would require less yeast extract, or which would eliminate the need for the yeast extract altogether, would not only further lessen the cost of operation but would also reduce possible contamination with extraneous microorganisms during the processing. Furthermore, the elimination of the yeast extract from the process would make it unnecessary to observe a stringent sterilization regimen, because very few microorganisms can grow in a medium which does not contain yeast extract.

In parallel developments major advances have also been made in processes wherein useful products have been accumulated within the fermentation medium, or culture broth. For example, since Imada and Yamada disclosed in 1962 the formation of amino acids from petroleum in a fermentation medium various microorganisms have been utilized for the production of amino acids. Kinoshita, e.g., has shown that, in the presence of a limited amount of biotin, L-glutamic acid can be produced in excellent yield by *Micrococcus glutamicus*. An improved process for the preparation of L-glutamic acid from carbohydrates by fermentation is disclosed in U.S. pat. No. 3,174,908 to Matsui et al. Among the species of disclosed bacteria capable of such action are certain species from the genera *Bacillus, Micrococcus, Brevibacterium, Corynebecterium,* and *Microbacterium.* There exists an increasing demand for monosodium glutamate as a flavoring agent, and it must be made from L-glutamic acid. Fermentation processes offer certain advantages over chemical processes for the production of L-glutamic acid. Fermentation processes which use microbial mutants produced by irradiation with cobalt or ultraviolet, e.g., has also been reported as useful for the production of L-lysine, L-valine, and L-ornithine, under well defined conditions with excellent yields.

Whereas much has been accomplished, and various microorganisms, inclusive particularly of the bacterium *Cellulomonas* (ATCC-21399) used alone or in symbiotic association with other microorganisms, have been successfully, reproducibly cultivated on various carbon or energy substrates, particularly cellulose, much might yet be done to provide greater yields of biomass at lesser cost, produce certain valuable by-products, particularly certain essential amino acids, and in general to accomplish such results with less complex growth mediums.

It is, accordingly, the primary objective of the present invention to provide a new and novel process which will provide these and other needs.

A particular object is to provide a new and novel process which will provide high yields of biomass from more simple nutrient media.

A more particular object is to provide a process of such character for the production of mutants of *Cellulomonas* ATCC-21399 which can be cultivated on a carbon substrate, or carbohydrate, but particularly cellulose, as a source of comestible, digestible protein.

A yet more specific object is to provide a new and novel process wherein such mutants provide protein of high nutrient value by the growth thereof in a simple medium which contains cellulose, but requires no yeast extract.

Yet another object is to provide a process of such character wherein the mutants during growth excrete certain amino acids, L-glutamic acid, L-lysine, and the like, within the culture broth, this providing major products due to the nature of the cellular biomass and as well, additional very valuable products which can be extracted or otherwise separated from the culture broth.

These and other objects are achieved in accordance with the present invention which, in general, contemplates (a) a process for the production or derivation by spontaneous or induced mutations from a parent microorganism of the genus *Cellulomonas* (ATCC-21399) of selected microbial mutants which, unlike the parent microorganism, have the ability to excrete certain amino acids, notably L-glutamic acid or L-lysine, or both;

(b) mutant strains produced by mutagenesis of the microorganism *Cellulomonas* (ATCC-21399) named and tabulated herein below along with their corresponding A.T.C.C. registration numbers, on deposit with the American Type Culture Collection in Washington, D.C., to wit:

| MICROORGANISM NAME | A.T.C.C. NO. |
|---|---|
| *Cellulomonas* sp. ATCC 21399 strain LC-10 | 31230 |
| *Cellulomonas* sp. ATCC 21399 strain A$^r$-1 | 31231 |
| *Cellulomonas* sp. ATCC 21399 strain A$^r$-156 | 31232 | the bacteriological characteristics of these microorganisms being determined by the below indicated tests leading to the above nomenclature are as follows:

| | Nomenclature Tests Tests, A.T.C.C. Number | | |
|---|---|---|---|
| | *Cellulomonas* sp. ATCC 21399 strain LC-10 (ATCC-31230) | *Cellulomonas* sp. ATCC 21399 strain A$^r$-1 (ATCC-31231) | *Cellulomonas* sp. ATCC 21399 strain A$^r$-156 (ATCC-31232) |
| Morphology | short rods | short rods | short rods |
| Motility | non-motile | non-motile | non-motile |
| Gram Reaction | | | |
| Agar Colony Morphology | smooth glistening | smooth glistening | smooth glistening |
| Carbohydrate Fermentation | starch hydrolized | starch hydrolized | starch hydrolized |
| Pigmentation | yellow in light | yellow in light | yellow in light |
| Gelatin Liquifaction | slow liqui-faction | slow liqui-faction | slow liqui-faction |
| Growth Temperature, °C | 25-35 C | 25-35 C | 25-35 C |
| Growth pH | 6.5-7.2 | 6.5-7.2 | 6.5-7.2 |
| Oxygen | aerobic | aerobic | aerobic |
| Resistance to: | | | |
| AEC (1) | − | + | + |
| L-Threonine | − | + | + |
| Excreted Compound: | | | |
| L-glutamic acid | + | + | − |
| Alanine | + | − | − |
| Asparagine | − | + | + |
| L-lysine | − | + | + |
| Remarks: | spontaneous mutant | induced mutant | induced mutant |

(1) AEC = S-(2-aminoethyl)-L-cystein and (c) a process for the preparation of comestible, digestible protein by the cultivation of a mutant strain of *Cellulomonas* (ATCC-21399) which has the ability to excrete L-glutamic acid or L-lysine, or both, preferably *Cellulomonas* sp. 21399 strain LC-10 (ATCC-31230), *Cellulomonas* sp. 21399 strain A$^r$-1 (ATCC-31231), or *Cellulomonas* sp. 21399 strain A$^r$-156 (ATCC-31232), using an aqueous nutrient medium, or culture broth, which contains assimilable sources of carbon, nitrogen and mineral nutrients.

Cultures of the microorganisms *Cellulomonas* sp. ATCC 21399 strain A$^r$-1, *Cellulomonas* sp. ATCC 21399 strain LC-10, and *Celluomonas* sp. ATCC 21399 strain A$^r$-156, supra, shall be maintained on deposit with the American Type Culture Collection during the pendency of the application. All restrictions on the availability of the culture deposit to the public will be irrevocably removed on the grant of a patent, and cultures will be maintained throughout the life of the patent.

In the practice of this invention, mutants of *Cellulomonas* (ATCC-21399) are first obtained which possess the property of excreting amino acids into an aqueous medium, or culture broth, when the microorganisms are grown in the presence of an assimilable source of carbon, and supplied with nitrogen and mineral nutrients. The mutant microorganisms themselves also constitute a source of bioprotein, the quality of which is unsurpassed by that produced by the parent microorganism. The rate of growth of the mutants is as high as that of the parent microorganism, but the nutritional requirements are far less exacting. In the use of cellulose as the carbon source, in particular, the cellulolytic activity of the mutants is as high as that of the parent microorganism, and likewise the nutritional requirements are far less exacting than in the cultivation of the parent organism. By directly growing the mutant microorganisms on cellulose in a more simple medium the cost of raw materials is considerably reduced, and greater process economies are realized because there is less contamination by other microorganisms since most other organisms cannot live in such medium. This means too, of course, that the need for a very stringent sterilization regimen is lessened.

The mutants useful in the practice of this invention are formed by mutation of the microorganism of the genus *Cellulomonas* (ATCC-21399), either by allowing the microorganism to undergo spontaneous mutation or by inducing mutations by the use of radiation or chemical mutagens, and the mutants are selected on the basis of their ability to excrete L-glutamic acid or L-lysine, or both. Both spontaneous and induced mutations are well known. Spontaneous mutations occur because of the ever present mutagens in the environment; these including cosmic radiation, radiation caused by radioactive compounds and naturally occuring ring base analogs, e.g., caffeine. The rate of such mutations can be increased, however, as by the use of heat and thermal agitation, heat being a physical mutagen which can cause occasional breakage of a thermally activated bond within the molecular structure of a DNA molecule, or an occasional ambiguity of base-pairing in replication. Mutation can also be induced by radiation, i.e., x-ray, ultra violet (UV), radioactive isomers, and the like. The chemical mutagens are comprised of several main types, i.e., (1) base analogs, (2) hydroxylamines, (3) nitrous acid, (4) alkylating agents, (5) acridine derivitives, and (6) nitrosoguanidine, Mn$^{++}$, of formaldehyde. The base analogs, the acridines, and Mn$^{++}$ require replication of DNA. The other mutagens, in contrast, are chemically reactive and alter DNA whether or not it is replicating. Exemplary of such mutagens are 5-bromouracil, 5-bromodeoxyuridine, 2-aminopurine, nitrous acid, sodium nitrite, hydroxylamine, ethylmethanesulfonate, ethylethanesulfonate, N-nitroso-N$^1$-nitro-methyl guanidine (NMNG), and the like.

The mutant microorganisms of this invention, whether produced spontaneously or induced, are always selected on the ability of a derived strain to excrete L-glutamic acid or L-lysine. In a preferred method of forming desirable mutants, mutant microorganisms are formed from *Cellulomonas* (ATCC-21399) by chemical or UV-irradiation induced mutations in a dilute aqueous solution, or broth containing the required nutrients at temperatures ranging from about 20° to about 40° C, preferably from about 30° to about 35° C, at pH ranging from about 4 to about 8, preferably from about 4 to about 6, during an incubation period ranging at least about 0.25 hours, suitably from about 0.25 to 4 hours, preferably from about 0.5 to about 2 hours. The desired strains are found by a replica plating technique wherein colonies, after contact with a mutagen, are transferred to a culture medium, e.g., an agar plate, and identified for their ability to excrete L-glutamic acid or L-lysine. The preferred strains are those which are capable of producing between about 0.1 to about 2 grams per liter of L-glutamic acid with a 1 to 2 percent carbon source, or between about 0.1 to about 1 gram per liter of L-lysine from a 1-2 percent carbon source.

The mutants can be cultivated on various energy or carbon substrates, alone or in compatable association with other microorganisms. Carbohydrates are also suitable, e.g., the monosaccharides such as glucose, and the like, the disaccharides such as sucrose, lactose, maltose and the like, and the polysaccharides such as the starches, celluloses, hemicelluloses and the like. Cellulose is a particularly preferred carbon source. Chemical celluloses, e.g., nitrocellulose, ethyl cellulose, cellulose acetate, methyl cellulose, carboxymethyl cellulose, and regenerated cellulose products, e.g., viscose, rayon, cupraammonium rayon, cellophane and the like, and particularly delignified cellulose from any source, e.g., bagasse, waste paper, etc., can be used as the energy or carbon substrate in accordance with this invention.

In the preferred embodiment, cellulose from any suitable source is first delignified, preferably by treatment with an alkali. Suitably, the cellulose is subjected to treatment by direct contact with an alkaline reagent or solution, preferably an aqueous solution of an alkali hydroxide, in concentration sufficient to partially hydrolyze or solvate the cellulose. Advantageously, tha alkali hydroxides are hydroxides of Group I metals of the Periodic Table of the Elements, e.g., sodium, lithium, potassium, and the like, sodium hydroxide being especially preferred because of its cheapness, wide availability and effectiveness. Preferably, the cellulose is treated with an aqueous alkali metal hydroxide solution, wherein the alkali metal hydroxide is present in concentration ranging from about 0.5 to about 75 percent, preferably from about 2 to about 20 percent, based on the weight of the total solution. Suitably, the physical size of the cellulose, if large, is reduced by cutting, sawing, grinding or crushing to assure intimate contact with the alkali. Generally, the cellulose is simply immersed in a solution of the alkali. Generally, the alkali treatment is conducted for periods ranging from about 0.1 hour to about 20 hours, or more, though time of treatment will vary in proportion to the kind, or nature, of the alkali used, its concentration or strength, the physical state, nature of the cellulose, its previous history of treatment, and upon the temperature of treatment. When using strong alkalis, e.g., alkali metal hydroxides such as sodium hydroxide, the alkali cellulose treatment is conducted at temperatures ranging from about −10° to about 70° C, preferably 10° to about 30° C, from about 1 to about 24 hours.

After contact between the cellulose and alkali, the treated cellulose is separated from the alkali by standard procedures known in the art, e.g., filtration, decantation, centrifugation, screening, passage between squeeze rolls, and the like. The alkali treated cellulose, generally after washing, is then placed in an oxidation, or circulating air oven and heated, generally at temperatures ranging from about −10° to about 150° C, and preferably at temperatures ranging from about 25° to about 100° C. The time period that the treated cellulose remains in the oven is not critical, periods generally ranging from about 0.1 to about 20 hours. Longer or shorter periods can be employed, the longer periods providing more complete digestion of the cellulose by the mutant microorganisms in a subsequent step. Generally, an optimum balance is maintained based on process economics. Air is blown on the cellulose during this period to accelerate the rate of oxidation and hydrolysis of the cellulose.

To initiate fermentation, the oxidized, alkali-treated cellulose is next removed from the oven, treated ex situ to a pH ranging between 5 and 9, e.g., a pH of 7, and then charged into a fermentor (or charged into the fermentor and then treated in situ to a pH ranging between 5 and 9). Adjustment of the pH is generally accomplished by addition of an aqueous acid solution, or proton donor, e.g., hydrochloric acid, with agitation sufficient to thoroughly contact the cellulose with the acid and establish equilibrium conditions. The temperature of the broth is then adjusted to that desired for the most rapid growth of the microorganism, suitably from about 20° to about 40° C. The fermentation medium is the inoculated with the mutant microorganism, or microorganisms, to be cultivated, and harvested. Within the fermentor, comprising a closed vessel, a draft tube and air lift are provided to maintain vigorous agitation and suitable aerobic conditions. The pH of the medium is maintained while providing optimum growth temperatures for the microorganisms to be harvested. If the pH becomes too high for optimum growth, it can be lowered by addition of a suitable acid to the fermentation media, or should the pH become too low, the pH can be raised by addition of a suitable base, e.g., ammonia, ammonium hydroxide, or sodium hydroxide.

The presence of oxygen is essential in the broth or cultivation medium. Oxygen can be supplied to the growth medium in any form capable of being assimilated readily by the inoculant microorganisms, and oxygen-containing compounds can be used as long as they do not adversely affect microorganism cell growth and conversion of cellulose to microorganism cells. Conveniently, however, the oxygen is supplied as an oxygen-containing gas, e.g., air, which contains from 19 to 22 wt. percent oxygen. While it is preferable to employ air, oxygen or oxygen enriched air, e.g., in excess of 22 wt. percent oxygen, can be used.

The presence of nitrogen is also essential to biosynthesis. The source of nitrogen can be any organic or inorganic nitrogen-containing compound which is capable of releasing nitrogen in a form suitable for metabolic utilization by the harvested microorganisms. In the organic category, the following compounds are listed as examplary nitrogen-containing compounds which can be used: proteins, acid-hydrolyzed proteins, enzyme-digested proteins, amino acids, yeast extract, asparagine, urea, and the like. A convenient and satisfactory method of supplying nitrogen is to employ ammonium phosphate or ammonium acid phosphate, which can be added as the salt, per se, or can be produced in situ in the aqueous fermentation media by bubbling ammonia through the broth to which phosphoric acid was previously added, thereby forming ammonium acid phosphate.

In addition to the energy and nitrogen sources, it is necessary to supply requisite amounts of selected mineral nutrients in the feed medium in order to insure proper microorganism growth and maximize selectivity, viz., the conversion of cellulose to microorganism cells. Thus, potassium, sodium, iron, magnesium, calcium, zinc, manganese, phosphorus, and other nutrients are included in the aqueous growth medium. These necessary materials can be supplied in the form of their salts, and preferably their water-soluble salts. For example, the potassium can be supplied as potassium chloride, phosphate, sulfate, citrate, acetate, nitrate, etc. Iron and phosphorus can be supplied in the form of sulfates and phosphates, respectively, e.g., iron sulfate, iron phosphate. Usually, most of the phorphorus is supplied as ammonia phosphates. When either ammonium phosphate or ammonium acid phosphate is used, it can serve as a combined source of both nitrogen and phosphorus (phosphate ion) for microorganism cell growth.

In a particularly preferred mode of practicing the present invention, high density cell cultures grown from mutants of Cellulomonas ATCC 21399, inclusive of other microorganisms grown in compatable association therewith, are produced by adding the carbon source and each of the other essential cell nutrients, incrementally or continuously, to the fermentation media, and maintaining each at essentially the minimum level needed for efficient assimilation by the growing cells in accordance with a pre-established cell growth curve based on the metabolic or respiratory function of the cells which convert the carbon source to a biomass. This technique is fully described in application Ser. No. 674,855 by Vadake R. Srinivasan et al. filed Apr. 8, 1976, which application is herewith incorporated by reference.

The invention will be better understood by reference to the following selected non-limiting examples and data which illustrate its more salient features. All parts are given in terms of weight units except as otherwise specified.

The following chemically defined medium, characterized in the examples as a minimal medium, has been found capable of supporting a satisfactory rate of growth of Cellulomonas sp ATCC 21399 strain LC-10. This simple medium, it will be observed, includes glucose as a carbon source, a mixture of salts, inclusive of trace salts, referred to hereinafter as a basic salt mixture (or basic salts), and specific vitamins in distilled water, to wit:

| | |
|---|---|
| Glucose | 5 g |
| $(NH_4)_2SO_4$ | 0.5 |
| $K_2HPO_4$ | 1.5 |
| $Na\ H_2PO_4$ | 0.5 |
| $MgCl_2 \cdot 6\ H_2O$ | 0.1 |
| $FeSO_4 \cdot 7\ H_2O$ | 0.005 |
| $CaCl_2 \cdot 2\ H_2O$ | 0.05 |
| Sodium citrate | 0.3 |
| Trace salts solution | 1 ml |
| Biotin | 5 ug |
| Thiamine | 10 ug |
| Distilled water | 1000 ml |
| Trace salts solution: | |
| $ZnSO_4 \cdot 5\ H_2O$ | 0.1 g |
| $CoCl_2 \cdot 6\ H_2O$ | 0.05 |
| $CuSO_4 \cdot 5\ H_2O$ | 0.005 |
| $MnCl_2 \cdot 6\ H_2O$ | 0.005 |
| Distilled water | 1000 ml |

In Example 1, immediately following, the parent microorganism, Cellulomonas sp ATCC-21399, was grown in such solution necessarily inclusive of an added yeast extract, and after separation of the mutant strain therefrom, it was found that the mutant microorganism, unlike the parent, could be grown in a medium which did not include the yeast extract.

EXAMPLE 1

Isolation and Growth of Cellulomonas sp. ATCC-21399 strain LC-10.

Cellulomonas sp. ATCC-21399 was grown overnight in a medium containing glucose, yeast extract and basic salt mixture. About $10^8$ organisms were spread on a number of plates containing 1.5% agar, 0.5% glucose, basic salts and vitamins. After 1 hour crystals of groups of amino acids were placed on the inoculated agar plates and incubated. After 3 days of incubation at 30° C a few colonies grew on one single group of amino acids, consisting of sienna, leucine and cystine. One such colony was isolated and grown in a liquid medium containing glucose (0.5%), vitamins (50 $\mu$g/ml), basic salts and the amino acids sienna, leucine, and cystine (100 $\mu$g/ml each). About $10^8$ organisms from such a culture were again spread on a plate containing 1.5% agar, glucose, vitamins and salts and incubated at 30° C for 3 days. Several colonies grew on such a plate. One such colony was isolated and purified by repeated streaking on a minimal agar plate and isolating a single colony. This strain of the Cellulomonas sp. 21399 is termed LC-10.

This strain was grown in different carbon sources in the medium outlined previously and the yield of cells is given in Table 1.

| Carbon Source | Volume of Fermentation | Time of Fermentation | Biomass Dry Wt., g/l |
|---|---|---|---|
| Glucose | 5 l. | 10 hr. | 29 |
| Solka Floc | 5 l. | 24 hr. | 18–20 |
| Bagasse | 5 l. | 36 hr. | 18 |

EXAMPLE 2

Isolation and Growth of Cellulomonas sp. ATCC-21399 strain A$^r$-1

Overnight grown cells Cellulomonas sp. ATCC-21399 strain LC-10 in minimal medium (liquid) were inoculated into a fresh medium for 7 hrs. at 30° C to obtain exponentially growing cells. The cells were harvested and re-suspended into 0.05 M Tris malate buffer (pH 6.0) at a cell concentration of $10^8$ ml. A 5 ml. suspension was mixed with 5 ml. of buffer solution containing 200 $\mu$g/ml of N-methyl-N-nitro-N'-nitros quanidine. After incubation at 30° C for 90 minutes, the cells were washed with sterile saline water twice and spread on the surface of the minimal agar containing 3 mg. of S. aminoethyl cystine (AEC). The colonies that appeared after 4–5 days at 30° C were isolated and repurified. The purified isolate was grown in a liquid minimal medium containing 3 mg/ml. of AEC. Glutamate excreting organisms from this culture were isolated as follows:

A strain of E. coli auxotrophic for glutamate was grown to late exponential phase in minimal medium supplemented with 100 $\mu$g/ml. of L-glutamate, washed twice with minimal medium and suspended at $10^9$ cells/ml. in the same medium without glutamate. One ml. cell suspension was added to 10 ml. of medium at 45° C containing 2% agar mixed and the mixture was immediately poured into a petri dish containing 10 ml.

of solidified minimal agar. After the agar hardened, appropriately diluted, AEC resistant organisms were mixed with soft agar (0.7% agar and minimal nutrients) and poured on the plates. The plates were incubated overnight. Approximately 1000 organisms on 20 plates were examined. The midlayer of agar exhibited a cloudy halo around strains excreting glutamic acids. Such colonies were isolated and purified. One such strain was designated as A$^r$-1. The A$^r$-1 organisms were grown as usual on different carbon sources and the glutamic acid in the medium was estimated enzymatically with glutamic dehydrogenase. Table II presents the results of such experiments.

Table II

| Carbon Source | Concentration | Time of Fermentation | Glutamic Acid |
|---|---|---|---|
| Glucose | 10 g/l. | 24 hr. | 3 g/l. |
| Solka Floc | 20 g/l. | 36 hr. | 7 g/l. |

EXAMPLE 3

Isolation of Cellulomonas sp. ATCC-21399 strain A$^r$-156 and Excretion of Lysine Overnight grown cells of the A$^r$-1 of Example 2 were treated with chemical mutagen MNMQ (nitroso methyl nitroquanidine) in a manner similar to that of LC-10 and plated on a medium containing 3 mg. of each of AEC and threonine. The plates were incubated at 30° C for 72 hrs. and the colonies were isolated and purified.

Lysine excreting strains were detached in a manner similar to the isolation of glutamic excretion with the aid of Lys auxotroph of *E. coli* instead of a glutamic acid auxotroph.

Several strains were examined and one strain, A$^r$-156, was grown in fermentors, and lysine was determined by colorimetric reaction with monohydrin after purification from the medium. Table III presents the amount of lysine excreted on different carbon sources.

Table III

| Carbon Source | Concentration | Time of Fermentation | Lysine |
|---|---|---|---|
| Glucose | 10 g/l. | 24 hr. | 0.5 g/l. |
| Solko Floc | 20 g/l. | 36 hr. | 1.2 g/l. |

It is apparent that this invention is subject to various modifications, as apparent to those skilled in this art, without departing the spirit and scope of the present invention.

Having described the invention, what is claimed is:

1. A process for the production of comestible, digestible protein which comprises cultivating a cellulase-elaborating bacterium of a mutant of Cellulomonas (ATCC-21399) which has the ability to excrete L-glutamic acid or L-lysine, or both, when the mutant microorganism is grown in a fermentation medium in the substantial absence of yeast extract on an assimilable source of carbon, and supplied with nitrogen and mineral nutrients, in the presence of oxygen at temperatures ranging from about 20° to about 40° C.

2. The process of claim 1 wherein the assimilable source of carbon is delignified cellulose.

3. The process of claim 2 wherein the delignified cellulose is formed by pretreatment of cellulose by contact with an alkali at temperature ranging from about −10° to about 70° C, for periods ranging from about 1 to about 24 hours.

4. A process for the production of comestible, digestible protein which comprises cultivating a cellulase-elaborating bacterium of a mutant microorganism of Cellulomonas (ATCC-21399) selected from the group consisting of:
Cellulomonas sp. ATCC-21399 strain LC-10 (ATCC-31230)
Cellulomonas sp. ATCC-21399 strain A$^r$-1 (ATCC-31231) and
Cellulomonas sp. ATCC-21399 strain A$^r$-156 (ATCC-31232)
which has the ability to excrete L-glutamic acid or L-lysine, or both, when the mutant microorganism is grown in a fermentation medium on an assimilable source of carbon, and supplied with nitrogen and mineral nutrients, in the presence of oxygen at temperatures ranging from about 20° to about 40° C.

5. The process of claim 4 wherein the assimilable source of carbon is delignified cellulose.

6. The process of claim 5 wherein the delignified cellulose is formed by pretreatment of cellulose by contact with an alkali at temperature ranging from about −10° C to about 70° C, for periods ranging from about 1 to about 24 hours.

7. A process for the production of L-glutamic acid or L-lysine, or both, by fermentation which comprises cultivating in an aqueous medium a cellulase-elaborating bacteria of a mutant produced by mutation of a bacterium of Cellulomonas (ATCC-21399), the mutant being selected and separated from dissimilar mutants on the basis of its unique ability to excrete L-glutamic acid or L-lysine, or both, said mutant strain being grown in a fermentation medium in the substantial absence of yeast extract on an assimilable source of carbon, and supplied with nitrogen and mineral nutrients, in the presence of oxygen at temperatures ranging from about 20° to about 40° C and recovering L-glutamic acid or L-lysine or both.

8. The process of claim 7 wherein the assimilable source of carbon is delignified cellulose, and wherein a comestible, digestible protein is coproduced with the L-glutamic acid or L-lysine, or both, by cultivation of the mutant on the delignified cellulose.

9. The process of claim 8 wherein the delignified cellulose is formed by pretreatment of cellulose by contact with an alkali at temperature ranging from about −10° to about 70° C, for periods ranging from about 1 to about 24 hours.

10. A process for the production of L-glutamic acid or L-lysine, or both, by fermentation which comprises cultivating a cellulase-elaborating bacterum of a mutant microorganism produced by mutation of a bacterium of Cellulomonas (ATCC-21399) selected from the group consisting of:
Cellulomonas sp. ATCC-21399 strain LC-10 (ATCC-31230),
Cellulomonas sp. ATCC-21399 strain A$^r$-1 (ATCC-31231), and
Cellulomonas sp. ATCC-21399 strain A$^r$-156 (ATCC-31232),
the mutant being selected and separated from dissimilar mutants on the basis of its unique ability to excrete L-glutamic acid or L-lysine, or both, said mutant strain being grown in a fermentation medium on an assimilable source of carbon, and supplied with nitrogen and mineral nutrients, in the presence of oxygen at temperatures ranging from about 20° to about 40° C.

11. The process of claim 10 wherein the assimilable source of carbon is delignified cellulose, and wherein a comestible, digestible protein is coproduced with the L-glutamic acid or L-lysine, or a mixture of L-glutamic acid an L-lysine.

12. The process of claim 11 wherein the delignified cellulose is formed by pretreatment of cellulose by contact with an alkali at temperature ranging from about −10° to about 70° C, for periods ranging from about 1 to about 24 hours.

13. In a process for the production of comestible, digestible protein by cultivation of a cellulase-elaborating bacterium of Cellulomonas (ATCC-21399) in the presence of oxygen in a medium which includes an assimilable source of carbon, nitrogen, yeast extract and mineral nutrients, the improvement which comprises:
   forming mutant strains by mutagenesis of the parent microorganism Cellulomonas (ATCC-21399), which have the ability to excrete L-glutamic acid or L-lysine, or both,
   separating from the medium a mutant which has the ability to excrete L-glutamic acid or L-lysine, or both,
   introducing said mutant into a medium, in the presence of oxygen at temperatures ranging from about 20° to about 40° C, and cultivating said mutant on delignified cellulose as an assimilable carbon source, while supplying said medium with nitrogen and mineral nutrients, without substantial addition of a yeast extract, to coproduce and recover comestible, digestible protein and L-glutamic acid or L-lysine, or a mixture of L-glutamic acid and L-lysine.

14. In a process for the production of comestible, digestible protein by cultivation of a cellulase-elaborating bacterium of Cellulomonas (ATCC-21399) in the presence of oxygen in a medium which includes an assimilable source of carbon, nitrogen, yeast extract and mineral nutrients, the improvement which comprises:
   forming mutant strains by mutagenesis of the parent microorganism Cellulomonas (ATCC-21399), which have the ability to excrete L-glutamic acid or L-lysine, or both,
   separating from the medium a mutant selected from the group consisting of:
   Cellulomonas sp. ATCC 21399 strain LC-10 (ATCC-31230),
   Cellulomonas sp. ATCC 21399 strain A$^r$-1 (ATCC-31231), and
   Cellulomonas sp. ATCC 21399 strain A$^r$-156 (ATCC-31232)
   which have the ability to excrete L-glutamic acid or L-lysine, or both,
   introducing said mutant into a medium, in the presence of oxygen at temperatures ranging from about 20° to about 40° C, and cultivating said mutant on delignified cellulose as an assimilable carbon source, while supplying said medium with nitrogen and mineral nutrients, to coproduce comestible, digestible protein and L-glutamic acid or L-lysine.

* * * * *